US006613570B2

(12) United States Patent
Knappe et al.

(10) Patent No.: US 6,613,570 B2
(45) Date of Patent: Sep. 2, 2003

(54) CONTROL LIQUID CONTAINING AN ADSORBENT

(75) Inventors: Wolfgang-Reinhold Knappe, Ludwigshafen (DE); Otto Gaa, Worms (DE); Volker Zimmer, Dossenheim (DE); Joachim Hoenes, Zwingenberg (DE); Bernd Hiller, Lampertheim (DE); Franz Wittmann, Hockenheim (DE); Beate Koschorreck, Schriesheim (DE)

(73) Assignee: Roche Diagnostics Corporation, Indianapolis, IN (US)

( * ) Notice: Subject to any disclaimer, the term of this patent is extended or adjusted under 35 U.S.C. 154(b) by 6 days.

(21) Appl. No.: 09/897,794

(22) Filed: Jun. 29, 2001

(65) Prior Publication Data

US 2002/0081740 A1 Jun. 27, 2002

(30) Foreign Application Priority Data

Jul. 3, 2000 (DE) ........................................ 100 32 290

(51) Int. Cl.$^7$ ................................................ G01N 31/00
(52) U.S. Cl. ........................ 436/14; 436/8; 252/408.1; 435/14
(58) Field of Search ............................ 436/8, 14, 16, 436/164, 169, 166, 180; 422/55, 56, 58, 100; 252/408.1; 435/14

(56) References Cited

U.S. PATENT DOCUMENTS

| 3,920,580 A | 11/1975 | Mast ........................... 252/408 |
| 4,451,563 A | 5/1984 | Kaufman ...................... 435/21 |
| 4,729,959 A | * 3/1988 | Ryan ........................... 436/14 |
| 5,187,100 A | 2/1993 | Matzinger et al. ............ 436/16 |
| 5,308,767 A | 5/1994 | Terashima .................... 436/12 |
| 5,360,803 A | * 11/1994 | Shishido et al. .......... 514/224.2 |
| 5,605,837 A | 2/1997 | Karimi et al. ................. 436/14 |
| 5,679,573 A | 10/1997 | Williams et al. ................ 436/8 |
| 5,725,774 A | * 3/1998 | Neyer ......................... 210/645 |
| 5,770,458 A | * 6/1998 | Klimov et al. ............... 436/518 |
| 5,998,488 A | 12/1999 | Shinohara et al. ........... 514/839 |

FOREIGN PATENT DOCUMENTS

| DE | 3788501 T2 | 4/1994 | |
| EP | 0127179 A1 | 12/1984 | |
| EP | 0266216 B1 | 5/1988 | |
| EP | 301847 | * 2/1989 | |
| EP | 0460896 B1 | 12/1991 | |
| EP | 0514485 B1 | 11/1992 | |
| WO | WO99/29429 | 6/1999 | |
| WO | WO99/30152 | 6/1999 | .......... G01N/33/48 |
| WO | WO99/30158 | 6/1999 | ......... G01N/33/543 |

OTHER PUBLICATIONS

Valentino J. Stella, et al., "Cyclodxtrins: Their Future in Drug Formulation and Delivery" Pharmaceutical Research, vol. 14, No. 5, 1997, (13 pgs).

* cited by examiner

*Primary Examiner*—Maureen M. Wallenhorst
(74) *Attorney, Agent, or Firm*—Jill L. Woodburn; Richard T. Knauer

(57) ABSTRACT

An aqueous control liquid is provided that contains glucose at a known concentration and cyclodextrin. A method is also provided that binds a wetting agent from a region of a test element that comes into contact with a sample. The method includes contacting the region with a control liquid that has a substance selected from the group of cyclodextrin derivatives and dispersed materials having a specific surface of 100 m$^2$/g to over 1000 m$^2$/g. A method for controlling the function of a measuring system having test strips and a measuring instrument for the determination of glucose in liquid samples is provided that includes contacting the test strip with a control liquid containing glucose at a known concentration and at least one substance selected from the group consisting of cyclodextrins and cyclodextrin derivatives and detecting a signal caused by the glucose contained in the control liquid.

9 Claims, No Drawings

CONTROL LIQUID CONTAINING AN ADSORBENT

The invention concerns a control liquid for the quality control and/or functional control of a measuring system comprising test strips and a measuring instrument for the determination of analytes in liquid samples.

The determination of the content of individual, usually low molecular metabolites in body fluids to check body functions has become an indispensable tool of modern medicine. Prominent examples are blood sugar self-monitoring by diabetics and recently the increasing measurement of the blood cholesterol content and the lactate concentration in blood, the latter being of particular importance in sports medicine to examine individual fitness.

Numerous carrier-bound test elements, so-called test strips, are now commonly used for reliable, rapid and uncomplicated analyses of body fluids and in particular of blood and urine. Simple test strips allow a visual determination of the concentration of the analyte of interest, for example by colour changes of a reagent layer on the test strip and comparison with a colour scale which is in turn correlated with analyte concentrations. Measuring systems which incorporate test strips and measuring instruments are more convenient. These systems detect the changes, usually photometrically or electrochemically, which result from the reaction of the analyte with the reagents which are present on or in the test strip.

Since it is not possible to manufacture batches of test strips that are 100% identical, it is necessary to make batch-specific calibrations of the measuring instruments. Nowadays this is usually carried out automatically by means of batch-specific codes which are read by the measuring instrument or are entered into the measuring instrument by the operator and which lead to an automatic adjustment by means of an evaluation algorithm for the measured values.

In addition to the manufacturing-dependent, batch-specific differences, the test strips and the measuring instruments are subject to variations in their measuring accuracy and reliability which for example can be caused by long or improper storage of the test strips or in the case of measuring instruments it may be due to the way they are used. Hence it is necessary to carry out a function and quality control of the measuring system at regular intervals in order to detect errors in time and if necessary to correct them. For this purpose manufactures of the measuring systems offer control liquids (synonym: control solutions) which are each specific for one measuring system.

The quality control and/or functional control of an analytical system comprising test strips and measuring instrument should ensure that the results of measurements obtained with the analytical system are always correct, accurate and reproducible. These are essential requirements especially for medical diagnostics which should provide the doctor with criteria for a specific therapy in order to reliably exclude wrong diagnoses or incorrect therapies.

The control liquids are usually essentially composed of aqueous buffer solutions of the analyte at a known predetermined concentration. However, they can also contain other additives which for example accurately imitate the viscosity or colour of the actual sample liquid in order to simulate measuring conditions that are as realistic as possible. Such control liquids are known for example from U.S. Pat. No. 3,920,580 and EP-B 0 514 485.

A control liquid is described in U.S. Pat. No. 3,920,580 in which so-called anti-diffusing agents such as bovine serum albumin, dextran and such like should make the control solution more like blood. This means that the test strip signal should be essentially the same for blood and the control solution at the same glucose concentration. EP-B 0 514 485 describes similar control liquids which contain polystyrene sulfonate or a salt thereof as a soluble polymer.

It is known from U.S. Pat. No. 5,679,573 that the steroid component of the control solution can be stabilized by the addition of cyclodextrins in the case of control liquids containing steroids. An influence of the cyclodextrin on the flow properties of the control solution is not described.

Recently more and more test systems are being sold in which the sample liquid is transported by means of a capillary (capillary channel, capillary gap etc.) from a sample application site to a distant measuring site on the test strip. Such test strips are described for example in WO 99/29429, WO 99/30158 or WO 99/30152. The surfaces of the capillary are often treated with a wetting agent in order to rapidly take up sample liquid and in particular blood or body fluids derived therefrom (plasma, serum) into the capillary of the test strip.

Of course the purpose of treating the capillary surface with wetting agents is to achieve optimal filling properties for the sample material such as blood. However, since the flow properties of control solutions can differ greatly from those of a blood sample, undesired effects can be observed when using capillary gap test strips in conjunction with control liquids: The control solution may possibly flow out of the capillary and thus contaminate or even destroy parts of the measuring instrument in which the test strip is placed for a measurement, or it may flow or drip from the test strip and thus contaminate the vicinity of the test strip (for example clothing, furniture etc.).

One method of circumventing the said problems would be to adjust the flow properties of a control solution to the flow properties of blood by adding an anti-diffusing agent like that described in U.S. Pat. No. 3,920,580. However, this is not always possible especially with glucose as the analyte (and thus glucose as the essential component of the control solution). For example in the presence of albumin which is recommended in U.S. Pat. No. 3,920,580 as a possible anti-diffusing agent, glucose present in a control solution is gradually and irreversibly bound to form glycated albumin and hence there is a continuous decrease of the glucose concentration during storage of the control liquid. However, this makes such a control solution of no use since the primary purpose of a control solution is to provide a defined constant concentration of a target analyte for a measurement in order to check the function of the measuring system.

There is a lack of control solutions in the prior art which solve the above-mentioned problem of uncontrolled flow in a capillary while maintaining a constant glucose concentration over long (storage) periods. Hence there is a need for control liquids which can provide a constant glucose concentration for a long period, typically 2 years, and which do not have a tendency to flow in an uncontrolled manner when used together with capillary gap test strips.

The object of the present invention was to eliminate the disadvantages of the prior art. In particular it is intended to provide control liquids which can provide a constant glucose concentration for a long time period, typically 2 years, and which do not have a tendency to flow in an uncontrolled manner when used together with capillary gap test strips.

This object is achieved by the subject matter of the invention as characterized in the patent claims.

The invention concerns an aqueous control solution containing glucose at a known concentration and at least one substance selected from the group comprising cyclodextrins, cyclodextrin derivatives and finely dispersed materials having a large specific surface.

The inventive control liquid or control solution is essentially an aqueous solution of glucose. The glucose is preferably present in the solution at a predetermined, known concentration. Common additives such as buffer substances, stabilizers, inorganic salts and such like can be added to this solution. When selecting the additives it is only important to ensure that the desired detection reaction of the test strip is not affected and in particular not negatively affected by them. For example in the case of optical detection systems, the additives should not have any effect on the colour development of the indicator substance. This applies analogously to electrochemical detection systems or enzymatic reactions which proceed on the test strip.

According to the invention the control liquid contains at least one substance selected from the group comprising cyclodextrins (i.e. α, β or γ cyclodextrin) or cyclodextrin derivatives, in particular their more water-soluble hydroxypropyl derivatives, and finely dispersed materials having a large surface which are to be understood as specific surfaces of 100 to over 1000 m²/g.

Although the mechanism of action of these substances when used for the inventive control solution has not been completely elucidated, their effect in the control solution is presumably based on the fact that they are able to at least partially bind wetting agents that are present in test strips to facilitate the wetting of the test strip by blood samples and thus to at least partially block their effect. Also worthy of mention is the fact that even highly viscous solutions which are only taken up slowly into a capillary gap test element have a tendency to flow in an uncontrolled manner without addition of the substances used according to the invention and thus could potentially contaminate the measuring instruments and/or the test element surroundings.

In a preferred embodiment the cyclodextrin derivative is hydroxypropyl-β-cyclodextrin. The degree of substitution of the cyclodextrin is not particularly important in this connection; in particular it is of no importance in the range of 0.6 to 1.0. Hydroxypropyl-β-cyclodextrin has proven to be particularly suitable because it is readily water-soluble without significantly increasing the viscosity of the control solution and hence the filling time, and is manufactured on a commercial scale. Hydroxypropyl-β-cyclodextrin is for example commercially available as CAVASOL®W7HP from the Wacker Chemie GmbH Company, Burghausen or Cavitron 82006 from the Cerestar Company, Krefeld. Other cyclodextrin derivatives are well-known to a person skilled in the art for example from V. J. Stella and R. A. Rajewski, Cyclodextrins: Their future in drug formulation and delivery, Pharm. Res. 14, 556–567 (1997).

In an alternative embodiment active charcoal or silicon dioxide (for example preferably in the form of Aerosil®) is used in the control liquid as a finely dispersed material having a large specific surface. However, such control solutions have a tendency to sediment and should therefore be shaken before use. Aerosil® is a highly dispersed pyrogenic silicic acid containing over 99.8% silicon dioxide which is produced by hydrolysis of silicon tetrachloride in an oxyhydrogen flame.

The control liquid according to the invention preferably contains the substance which is selected from the group comprising cyclodextrins, cyclodextrin derivatives and finely dispersed materials having a large specific surface at a concentration of 5 mg/ml to 50 mg/ml.

Concentrations of 5 to 50 mg/ml have proven to be preferable for cyclodextrins or derivatives thereof. Concentrations of 5 to 20 mg/ml are preferred for finely dispersed materials having a large specific surface such as active charcoal or silicon dioxide (Aerosil).

Although it is preferable to use only one substance in the control liquid which is selected from the group comprising cyclodextrins, cyclodextrin derivatives and finely dispersed materials having a large specific surface, it is also possible to use more than one of the said substances.

A further subject matter of the invention is the use of a control liquid according to the invention as described above for the quality and/or the functional control of a system comprising test strips and measuring instrument, and a method for controlling the function of a measuring system comprising test strips and measuring instrument for the determination of glucose in liquid samples comprising contacting the test strip of the measuring system with a control liquid according to the invention and detecting the signal caused by the glucose contained in the control liquid. This signal can be a colour formation or colour change which is caused by interaction of appropriate detection reagents on the test strip with the analyte (glucose); in this case the measuring instrument can monitor the colour change by for example reflection photometry. However, the signal can also be a change in an electrical property of the sample and/or the test strip which can be recorded by the measuring instrument. For example the measuring system can operate amperometrically or potentiometrically. All these methods are known to a person skilled in the art.

Finally the invention concerns the use of a substance selected from the group comprising cyclodextrins, cyclodextrin derivatives and finely dispersed materials having a large specific surface in a control liquid (having the meanings and preferred forms described above) to bind a wetting agent from a region of a test element that comes into contact with the sample. In this case the wetting agent can for example be bound by adsorption to the surface of one of the said substances as is the case for example for finely dispersed materials having a large specific surface or by inclusion of the wetting agent into appropriate substances for example cyclodextrins or derivatives thereof. The exact mechanism of action is of secondary importance for the present invention. It is only important that the wetting agent is at least partially bound and thus its function is inactivated and in this manner the flow properties of the control solution are adjusted to those of a real sample (e.g. blood in which albumin may be responsible for the inactivation of the wetting agent which turned out to be the case during the course of the investigations for the present invention). The corresponding regions of the test element or test strip which come into contact with the sample and contain a wetting agent can for example be a capillary channel for sample transport, a layer of spreading agent, a sample application zone in the form of an absorbent material or a well, a detection layer containing reagents or such like. A person skilled in the art knows which regions of a test strip/test element can come into contact with the sample (sample liquid) and can contain wetting agents.

The invention is elucidated in more detail by the following examples.

EXAMPLE 1

Glucose Control Liquids

A glucose control liquid (=KF 1) containing hydroxypropyl-β-cyclodextrin was mixed together from the ingredients stated in the following table 1. A glucose control liquid without hydroxypropyl-β-cyclodextrin (hydroxypropyl-β-CD) (=KF 2) was prepared for the purposes of comparison and was identical to the glucose control liquid containing hydroxypropyl-β-cyclodextrin apart from the amount of water. Other control liquids according to the invention were prepared by dispersing 1.4% Aerosil® 380 (=KF 3) or 1% Pulsorb® GW (=KF 4) both from the Degussa AG, Frankfurt/Main, in KF 2.

TABLE 1

| | amount [g] | | | |
|---|---|---|---|---|
| Ingredient | KF1 | KF2 | KF3 | KF4 |
| redistilled water | 80.60 | 82.60 | 81.20 | 81.60 |
| $KH_2PO_4$ | 0.26 | 0.26 | 0.26 | 0.26 |
| $Na_2HPO_4$ | 0.54 | 0.54 | 0.54 | 0.54 |
| 2-hydroxypyridine-N-oxide | 0.10 | 0.10 | 0.10 | 0.10 |
| Germal 115[1] | 0.10 | 0.10 | 0.10 | 0.10 |
| Kathon CG[2] | 0.10 | 0.10 | 0.10 | 0.10 |
| glucose | 0.30 | 0.30 | 0.30 | 0.30 |
| Macrogol 6000[3] | 3.50 | 3.50 | 3.50 | 3.50 |
| glycerol | 12.50 | 12.50 | 12.50 | 12.50 |
| hydroxypropyl-β-CD | 2.00 | 0 | 0 | 0 |
| Aerosil 380 | 0 | 0 | 1.40 | 0 |
| Pulsorb GW | 0 | 0 | 0 | 1.00 |
| Total | 100 | 100 | 100 | 100 |

[1]N,N"-methylenebis-(N'-(hydroxymethyl)-2,6-dioxo-4-imidazolinyl urea) from the ISP Glibal Technologies Company, Frechen
[2]mixture of 5-chloro-2-methylisothiazolo-3-one and 2-methylisothiazolo-3-one from the C. H. Ebersloeh Company, Krefeld
[3]polyethylene glycol with an average molar mass of 6000 from the Clariant Company (Germany) GmbH, Frankfurt/Main

EXAMPLE 2

Use of the Control Liquids with a Capillary Gap Test Element Placed Horizontally 15 μl of each of the control liquids from example 1 (KF 1 and KF 2) were applied to the sample application opening of a capillary gap test element as described in FIG. 1 of WO 00/19185 placed horizontally on a solid support. The notch of the sample application opening faced upwards. The control liquid was taken up by capillary forces into the capillary gap (capillary channel) of the test element until this was filled. The remainder of the control liquid remained as a small droplet on the sample application opening. It was observed in how many cases the applied control liquid emerged after 10 min from the end of the capillary gap (air bleed hole) opposite to the sample application opening. It is desirable that no control liquid emerges from the vent opening.

In the case of the control liquid (KF 1 from example 1) according to the invention, there was no discharge of control liquid from the vent opening after 10 min in any of the 51 examined cases (corresponds to 0%) and the same was observed with KF 3 and KF 4.

In the case of the conventional control liquid (KF 2 from example 1) discharge of control liquid from the vent opening was already observed after 1 min in 45 of the 50 examined cases (corresponds to 90%) and in all cases after 10 min.

Note: In none of the cases was a discharge from the vent opening observed with blood as the sample liquid.

EXAMPLE 3

Use of the Control Liquids with a Capillary Gap Test Element Held Obliquely

15 μl of each of the control liquids from example 1 (KF 1 and KF 2) were applied to the sample application opening of a capillary gap test element as described in FIG. 1 of WO 00/19185 placed horizontally on a solid support. The notch of the sample application opening faced upwards. The control liquid was taken up by capillary forces into the capillary gap (capillary channel) of the test element until this was filled. The remainder of the control liquid remained as a small droplet on the sample application opening. Afterwards the test element was tilted so that the sample application opening pointed upwards and the test element was at an angle of ca. 20 to 25° to the horizontal support. It was observed in how many cases the applied control liquid emerged after 10 min from the end of the capillary gap (air bleed hole) opposite to the sample application opening. It is desirable that no control liquid emerges from the vent opening.

With the control liquid according to the invention (KF 1 from example 1) a discharge of the control liquid from the vent opening was observed in 6 of the 51 examined cases (corresponding to 12%) after 10 min. Also in this case KF 3 and KF 4 exhibited a similar behaviour in which 8 of 50 (=16%) or 6 of 50 (=12%) cases a discharge was observed.

In the case of the conventional control liquid (KF 2 from example 1) discharge of control liquid from the vent opening was already observed after 1 min in 50 of the 50 examined cases (corresponds to 100%).

Note: In none of the cases was a discharge from the vent opening observed with blood as the sample liquid.

What is claimed is:

1. Aqueous control liquid containing glucose as a known concentration and a cyclodextrin selected from the group consisting of α, β and γ cyclodextrin.

2. Control liquid as claimed in claim 1, wherein the cyclodextrin is present at a concentration of 5 mg/ml to 50 mg/ml.

3. Method of binding a wetting agent from a region of a test element that comes into contact with a sample comprising contacting the region of the test element that comes into contact with the sample with a control liquid that comprises glucose and a substance selected from the group consisting of cyclodextrin derivatives and dispersed materials having a specific surface of 100 $m^2$/g to over 1000 $m^2$/g, wherein the control liquid serves to at least partially bind a wetting agent located in said region of said test element.

4. Method as claimed in claim 3, wherein the cyclodextrin derivative is hydroxypropyl-β-cyclodextrin.

5. Method as claimed in claim 3, wherein the substance selected from the group consisting of cyclodextrin derivatives and dispersed materials having a specific surface of 100 $m^2$/g to over 1000 $m^2$/g is present at a concentration of 5 mg/ml to 50 mg/ml.

6. Method of binding a wetting agent from a region of a test element that comes into contact with a sample comprising contacting the region of the test element that comes into contact with the sample with a control liquid that comprises glucose and a substance selected from the group consisting of cyclodextrin derivatives and dispersed materials having a specific surface of 100 $m^2$/g to over 1000 $m^2$/g, wherein the control liquid serves to at least partially bind a wetting agent located in said region of said test element and the dispersed material having a specific surface of 100 $m^2$/g to over 1000 $m^2$/g is active charcoal or silicon dioxide.

7. Method for controlling the function of a measuring system comprising a test strip and a measuring instrument for the determination of glucose in liquid samples comprising contacting the test strip of the measuring system with a control liquid containing glucose at a known concentration and at least one substance selected from the group consisting of cyclodextrins and cyclodextrin derivatives and detecting a signal caused by the glucose contained in the control liquid.

8. Method as claimed in claim 7, wherein the cyclodextrin derivative is hydroxypropyl-β-cyclodextrin.

9. Method as claimed in claim 7, wherein the substance selected from the group consisting of cyclodextrins and cyclodextrin derivatives is present at a concentration of 5 mg/ml to 50 mg/ml.

* * * * *